United States Patent [19]

Guadalupi et al.

[11] 4,137,262

[45] * Jan. 30, 1979

[54] PROCESS FOR THE PRODUCTION OF UREA

[75] Inventors: Mario Guadalupi, Milan; Umberto Zardi, San Donato Milanese; Vincenzo Lagana, Milan, all of Italy

[73] Assignee: Snam Progetti S.p.A., Milan, Italy

[*] Notice: The portion of the term of this patent subsequent to Oct. 5, 1993, has been disclaimed.

[21] Appl. No.: 696,405

[22] Filed: Jun. 15, 1976

Related U.S. Application Data

[63] Continuation of Ser. No. 477,048, Jun. 6, 1974, Pat. No. 3,984,469, which is a continuation of Ser. No. 81,475, Oct. 16, 1970, abandoned.

[30] Foreign Application Priority Data

Oct. 16, 1969 [IT] Italy ............................ 23440 A/69

[51] Int. Cl.² .......................................... C07C 126/02
[52] U.S. Cl. ............................................... 260/555 A
[58] Field of Search ........................ 260/555 A, 555 R

[56] References Cited

U.S. PATENT DOCUMENTS

| | | | |
|---|---|---|---|
| 3,120,563 | 2/1964 | Bongard | 260/555 A |
| 3,607,938 | 9/1971 | Braun | 260/555 A |
| 3,984,469 | 10/1976 | Guadalupi et al. | 260/555 A |

OTHER PUBLICATIONS

Urea Process Technology, 1968, Powell, pp. 136–142.

*Primary Examiner*—Edward J. Meros

[57] ABSTRACT

A process for producing urea from $CO_2$ and $NH_3$ in which the $CO_2$ and $NH_3$ are reacted in a reactor, the reaction product containing unreacted carbamate, $CO_2$, $NH_3$ and water is passed into a first decomposer maintained at the same pressure as the reactor, the reaction product is heated and thermally decomposed in said first decomposer to separate a major amount of carbamate from the reaction product, the remaining reaction product is passed into the upper end of a second decomposer maintained at the same pressure as the reactor and first decomposer and said remaining reaction product in said second decomposer is contacted with a stripping stream of inert gas, separating the unreacted compounds from the liquid effluent and a finished product comprising a water solution of substantially pure urea is removed from the lower end of the second decomposer.

4 Claims, 1 Drawing Figure

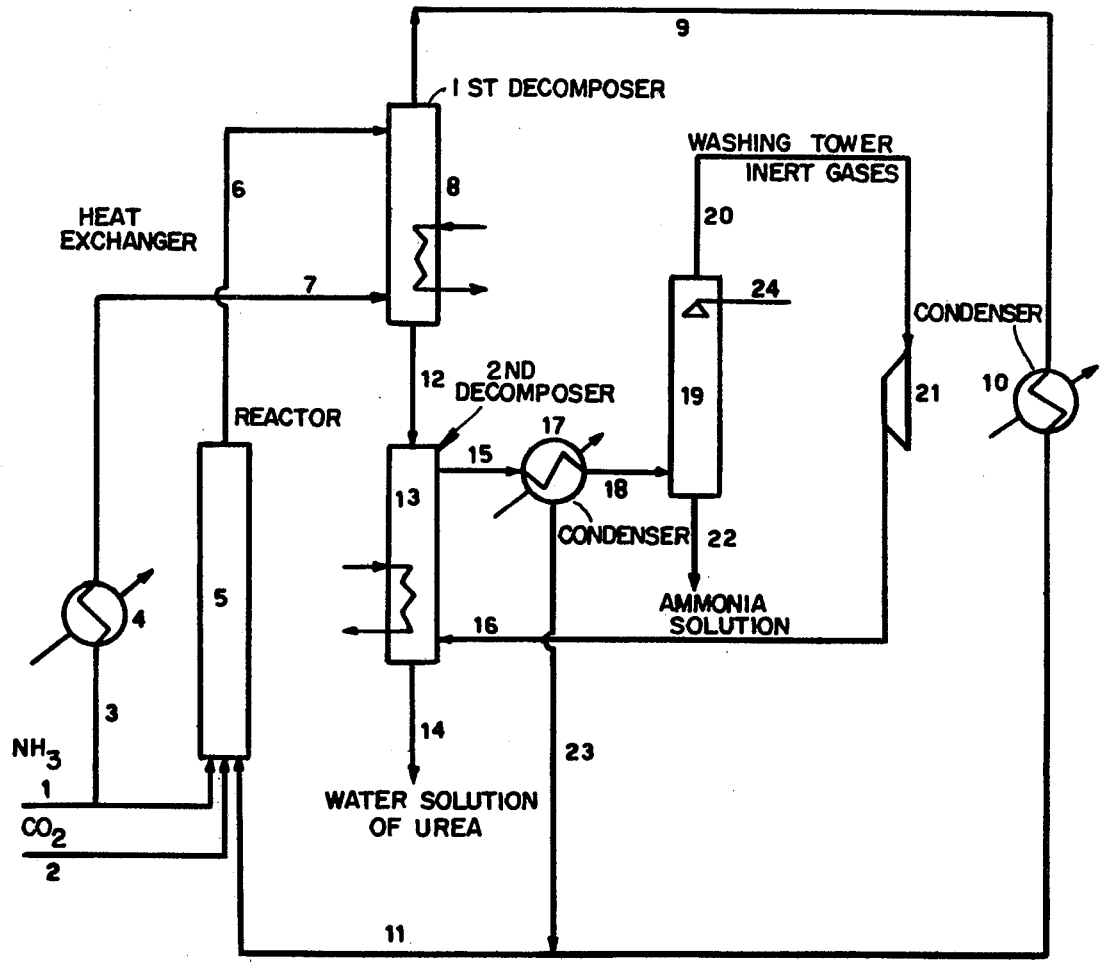

PROCESS FOR THE PRODUCTION OF UREA

This is a continuation of application Ser. No. 477,048 filed June 6, 1974, now U.S. Pat. No. 3,984,469 in turn a continuation of application Ser. No. 81,475 filed 16, 1970, now abandoned.

This invention relates to a process for the production of urea.

It is known that a new technology developed in the last years in the field of urea production, which allowed a remarkable reduction in the investment and operation costs. On the ground of such new technology the carbamate contained in the effluents, coming from the reactor, dissociates and separates from the solution of urea by means of a stripping agent at a total pressure which may be also the one of the synthesis. It was trying to avoid the thermic decomposition at low pressure.

Said new processes allowed considerable reduction of the product cost; in effect they permit, as it is known, to recover the heat developed in the condensation of the effluents coming from the carbamate decomposition, generating steam which may be reused in other zones of the plant.

According to the above cited technology the stripping agents may be $NH_3$ and $CO_2$. In the process employing $NH_3$ as stripping agent there is the elimination practically complete of the $CO_2$ contained in the stream coming out from the reactor; anyhow an appreciable amount of $NH_3$ remains in such stream.

In the process employing $CO_2$ as stripping agent there is in the stream coming out from the decomposer, a residual content of $NH_3$ lower, compared with the process before mentioned, but an appreciable residue of $CO_2$.

Therefore it is a matter of course that notwithstanding the remarkable advantages, both the processes require onerous sections for the final treatment of the solution, both for recovering quantitatively $NH_3$ and $CO_2$ to send back to the synthesis and for obtaining an aqueous solution of urea free from $CO_2$ and from $NH_3$. It is at the same time known the techniques which provide decomposing thermically without employing a stripping agent.

The object of this invention is a proces which permits of eliminating the above drawbacks realizing the whole recycle of all residual compounds contained in the effluents of the reactor (carbamate, carbonates, $NH_3$) through a system operatng preferably at the same pressure of the reactor, obtaining a practically pure aqueous solution of urea.

A further object of this invention is a method for the complete purification of the solution coming from the reactor. In the process, object of the present invention, a stream of $NH_3$ and of $CO_2$ is conveyed into a reactor. The reaction mixture is maintained under a pressure ranging from 50 to 300 atmospheres and at a temperature ranging from 150 to 300° C.; the mixture coming out from the reactor and composed of urea, carbamate, ammonia, carbon dioxide and water is forwarded to a decomposer of carbamate operatinhg substantially at the synthesis pressure. Said decomposer may operate as a simple distillator (without any stripping agent) or letting flow in countercurrent to the cited solution a stream of an overheated gaseous ammonia, which sent as stripping agent favours the total decomposition of the carbamate.

In the first case a simple thermic decomposition occurs. The carbamate decomposer, also in the case there is a stripping agent, is heated for furtherly favouring the decomposition.

The gaseous stream coming out from the top of the carbamate decomposer, essentially constituted by $NH_3$, $CO_2$ and $H_2O$, is condensed in a condenser wherein steam is generated at high thermic level, which may be re-utilized in other parts of the plant. The condensed phase coming out from the condenser is recycled to the synthesis zone. The liquid phase coming from the bottom of the decomposer practically $CO_2$ free, is forwarded to a second decomposer wherein an inert gas ($N_2$, $N_2$ and $H_2$ and/or other ones) is employed as a stripping agent. Also the second decomposer is heated and operates substantially at the synthesis pressure.

The gaseous stream coming out from the second decomposer essentially containing the inert saturated with $NH_3$ and $H_2O$ is sent into a condenser where the heat is recovered generating steam at high thermic value. The part which condenses is recycled to the synthesis, while the inert not condensed, if that is the case, is forwarded to a washing for recovering the $NH_3$ still contained. From such a washing the inert comes out practically pure and after being compressed again it is recycled to the second decomposer as reported before. From the bottom of the second decomposer a water solution of practically pure urea comes out, which goes to the following treatments.

It is obvious the advantage of operating, in any part, of the plant, at a pressure equal to the synthesis one. As a matter of fact, besides vapours to be condensed at high pressure, which permit to produce steam usable in the different parts of the plant, there is a remarkable simplification of the process control and the number of the apparatuses necessary, if different values of pressure were utilized, is reduced.

Furtherly, as high re-compressions are not necessary there are low consumptions of energy, which in this part of the plant are reduced to the necessary ones for the circulation of the inert gas stream.

Hereinafter a detailed description of this invention process is reported, referring to the particular case wherein in the first decomposer a stripping by means of ammonia is performed.

In the drawing 1 there is the scheme of the process which has already been briefly described. With reference to said drawing through lines 1 and 2, respectively, $NH_3$ and $CO_2$ reach to reactor 5.

The synthesis products, essentially constituted by urea, carbamate, $NH_3$, $CO_2$ and water, through line 6 are sent to the first decomposer in countercurrent with ammonia. Said ammonia is drawn from line 1 through line 3, vapourized and overheated in the heat exchanger 4 and through line 7 sent to the decomposer 8. In the decomposer 8 the carbamate decomposition occurs because of the heating and of the stripping action of the ammonia.

The vapours coming out from the top of the decomposer through line 9 are forwarded to the condenser 10, wherein steam is produced and the condensed phase is recycled through line 11 to the synthesis.

From the decomposer 8 through line 12 urea solution substantially $CO_2$ free enters from the top the second decomposer 13 and meets in countercurrent the inert gas introduced in the bottom of the decomposer 13 through line 16. The consequent stripping frees the solution from the whole ammonia; in such a way from the bottom of decomposer 13 a water solution of urea substantially pure is withdrawn and goes to the following treatments through line 14. The mixture of gases and vapours coming out from the top of the decomposer 13 and formed essentially of $NH_3$, inert steam goes, through line 15, to the condenser 17; the condensed part is introduced through line 23 into line 11 and then recycled to the synthesis, the uncondensable gases so through line 18 to the washing tower 19 and meet in countercurrent the washing liquid introduced through line 24.

From the bottom of tower 19 a water solution of ammonia comes out through line 22, from the top come out the purified inert gases, which through 20 go to the compressor 21 and through 16 come back to the bottom of the decomposer 13 for the stripping.

A great number of possible realizations of the scheme are obviously feasible with reference to the system of purifying inert gas, which is made to circulate in the stripper 13, and as to the operative pressure of the different apparatuses such as the reactor 5, the decomposers of the carbamates 8 and 13, the condenser of carbamate 10 a.s.o.

An important modification of the scheme reported in drawing 1, may be realized by allowing to work the first decomposer without any stripping agent, i.e. by carrying out in such stage a simple thermic decomposition. In such a case, referring to the scheme of drawing 1, lines 3 and 7 and the heat exchanger 4, are missing.

A further important modification of the scheme of drawing 1 is realized by sending to the decomposer 13, as a stripping agent, an inert gas coming from an external source, which may be recycled to the above mentioned external source after being subjected to a possible purification treatment. For instance possible $N_2 + 3H_2$ coming from a plant of preparation of the mixture for the ammonia synthesis are sent. In this case, with reference to FIG. 1, lines 15 and 16 are opportunely connected to such a plant. Effectively it is desirable that near a plant for the urea production there be a plant for the ammonia synthesis.

Since it is completely obvious that modifications and variations may be effected to the preceding description without deviating from the nature and the spirit of the invention, it must be well understood that this one is not limited by this description.

Now we report an example which is supplied with the aim of illustrating the present invention without constituting a limitation of the same. Only in the case it is not indicated in a different way, all the percentages expressed in the description are given by weight.

EXAMPLE 1

With reference to the scheme of drawing 1 in line 6 there is a reaction mixture of the following composition:

| | |
|---|---|
| $NH_3$ | 40.0% |
| $CO_2$ | 14.0% |
| $CO(NH_2)_2$ | 29.0% |
| $H_2O$ | 17.0% |
| | 100.0 |

After the passage of said mixture into the decomposer 8 there are the following compositions in the line 12:

| | |
|---|---|
| $NH_2$ | 27.0% |
| $CO_2$ | 2.0% |
| $CO(NH_2)_2$ | 40.0% |
| $H_2O$ | 31.0% |
| | 100.0 |

The liquid of the above composition is let pass through the decomposer 13 and from line 14 a mixture of the following composition comes out:

| | |
|---|---|
| $NH_3$ | 0.5% |
| $CO_2$ | 0.5% |
| $CO(NH_2)_2$ | 76.2% |
| $H_2)$ | 22.8% |
| | 100.0 |

It is obvious the excellent purification obtainable by means of such process; excellent purification which means obviously an excellent recovery of the product which did not react.

We claim:

1. A process for the production of urea from $CO_2$ and $NH_3$ which comprises reacting $CO_2$ and $NH_3$ in a reactor to form a liquid reaction product containing unreacted carbamate, $CO_2$, $NH_3$ and water, passing said liquid reaction product containing said unreacted carbamate, $CO_2$, $NH_3$ and water into the upper end of a first stage decomposer maintained at substantially the same pressure as said reactor, in the absence of a stripping agent heating said liquid reaction product and said water in said first stage decomposer and thermally decomposing and separating a major amount of carbamate from said liquid reaction product in said first stage decomposer, passing the liquid effluent remaining after said thermal decomposition and separation in said first stage decomposer from the lower end of said first stage decomposer into the upper end of a second stage decomposer maintained at substantially the same pressure as said reactor and said first stage decomposer and separating the unreacted compounds from said liquid effluent by contacting said liquid effluent in said second stage decomposer with a stripping stream of inert gas and removing from the lower end of said second stage decomposer, as finished product, a water solution of substantially pure urea.

2. A process for the production of urea as recited in claim 1 wherein a mixture of said inert gas and $NH_3$ are withdrawn from the upper end of said second stage decomposer and said mixture is passed to a condenser where said inert gas is separated from said $NH_3$ and said $NH_3$ is passed to said reactor.

3. A process as recited in claim 1 wherein the reactor pressure is not substantially less than 50 and not substantially more than 300 atmospheres.

4. A process as recited in claim 2 wherein the reactor pressure is not substantially less than 50 and not substantially more than 300 atmospheres.

* * * * *